US008725801B2

(12) United States Patent
Kariathungal et al.

(10) Patent No.: US 8,725,801 B2
(45) Date of Patent: May 13, 2014

(54) SYSTEMS AND METHODS FOR IMAGE SHARING IN A HEALTHCARE SETTING WHILE MAINTAINING DIAGNOSTIC IMAGE QUALITY

(75) Inventors: Murali Kumaran Kariathungal, Hoffman Estates, IL (US); Prakash Mahesh, Hoffman Estates, IL (US)

(73) Assignee: General Electric Company, Schenectady, NY (US)

( * ) Notice: Subject to any disclaimer, the term of this patent is extended or adjusted under 35 U.S.C. 154(b) by 1089 days.

(21) Appl. No.: 11/602,785

(22) Filed: Nov. 21, 2006

(65) Prior Publication Data

US 2008/0120372 A1 May 22, 2008

(51) Int. Cl.
*G06F 15/16* (2006.01)
(52) U.S. Cl.
USPC .......... 709/204; 709/209; 715/765; 715/275; 715/753; 345/601
(58) Field of Classification Search
USPC ......... 715/209, 765, 730, 151, 175, 275, 753; 382/154, 282, 232, 243; 709/218, 231, 709/204, 209; 345/1.1, 601, 619, 751; 703/25; 705/37; 710/8
See application file for complete search history.

(56) References Cited

U.S. PATENT DOCUMENTS

| | | | |
|---|---|---|---|
| 5,335,323 A * | 8/1994 | Kolnick | 715/765 |
| 5,513,278 A * | 4/1996 | Hashizume et al. | 382/187 |
| 5,893,127 A * | 4/1999 | Tyan et al. | 715/209 |
| 5,986,622 A * | 11/1999 | Ong | 345/1.1 |
| 6,083,167 A * | 7/2000 | Fox et al. | 600/439 |
| 6,101,407 A | 8/2000 | Groezinger | |
| 6,260,021 B1 * | 7/2001 | Wong et al. | 705/2 |
| 6,385,566 B1 * | 5/2002 | Tillery, Jr. | 703/25 |
| 6,400,380 B1 * | 6/2002 | Ansberry et al. | 715/753 |
| 6,535,630 B1 * | 3/2003 | Saeki | 382/162 |
| 6,711,297 B1 * | 3/2004 | Chang et al. | 382/240 |
| 6,934,737 B1 * | 8/2005 | Tang et al. | 709/204 |
| 7,145,992 B2 * | 12/2006 | Orikasa et al. | 379/93.29 |
| 7,222,305 B2 * | 5/2007 | Teplov et al. | 715/751 |
| 7,439,937 B2 * | 10/2008 | Ben-Shachar et al. | 345/1.1 |
| 7,568,005 B2 * | 7/2009 | Nichols et al. | 709/204 |
| 7,583,843 B2 * | 9/2009 | Mossakowski | 382/232 |
| 7,599,989 B2 * | 10/2009 | Stevens et al. | 709/204 |
| 7,804,497 B2 * | 9/2010 | Song et al. | 345/204 |

(Continued)

OTHER PUBLICATIONS

Bala et al. Information-Preserving Imaging for Heterogeneous Networked Displays. Apr. 2006. ACM.*

(Continued)

*Primary Examiner* — Anthony Mejia

(57) ABSTRACT

Certain embodiments of the present invention provide a method for image sharing and display. The method includes selecting an image, establishing a context with a peer workstation, and displaying an image on the peer workstation based on the established context. The context may include an image sharing coordinate system, the displayed data types, the coordinates of displayed data types, and lookup tables for image data types. Certain embodiments of the present invention provide a system for image sharing and display. The system includes a master workstation and a peer workstation. The peer workstation includes a display device adapted to display an image based at least in part on information received from the master workstation. The information received from the master workstation may include an image sharing coordinate system, the displayed data types, the coordinates of displayed data types, and lookup tables for image data types.

17 Claims, 3 Drawing Sheets

(56) References Cited

U.S. PATENT DOCUMENTS

| | | | | |
|---|---|---|---|---|
| 7,925,797 | B2* | 4/2011 | Wolff-Peterson | 710/8 |
| 8,005,571 | B2* | 8/2011 | Sutherland et al. | 700/248 |
| 8,244,824 | B2* | 8/2012 | Garibaldi et al. | 709/208 |
| 8,310,529 | B2* | 11/2012 | Krupnick et al. | 348/65 |
| 2002/0159653 | A1* | 10/2002 | Dekel et al. | 382/282 |
| 2002/0165813 | A1* | 11/2002 | Lee | 705/37 |
| 2003/0005140 | A1* | 1/2003 | Dekel et al. | 709/231 |
| 2003/0059096 | A1* | 3/2003 | Dekel et al. | 382/131 |
| 2003/0107594 | A1* | 6/2003 | Bennett et al. | 345/760 |
| 2003/0128198 | A1* | 7/2003 | Mizuyabu et al. | 345/204 |
| 2003/0152262 | A1* | 8/2003 | Mao et al. | 382/154 |
| 2004/0179036 | A1* | 9/2004 | Teplov et al. | 345/751 |
| 2004/0252129 | A1* | 12/2004 | Pallister | 345/601 |
| 2005/0089214 | A1* | 4/2005 | Rubbert et al. | 382/154 |
| 2005/0259882 | A1* | 11/2005 | Dewaele | 382/243 |
| 2005/0267972 | A1 | 12/2005 | Costa-Requena et al. | |
| 2005/0271283 | A1* | 12/2005 | Dekel et al. | 382/232 |
| 2006/0038740 | A1* | 2/2006 | Jung et al. | 345/1.1 |
| 2006/0109237 | A1* | 5/2006 | Morita et al. | 345/156 |
| 2006/0114351 | A1* | 6/2006 | Tanigawa | 348/441 |
| 2006/0167997 | A1* | 7/2006 | Forstadius | 709/204 |
| 2006/0168532 | A1* | 7/2006 | Stevens et al. | 715/753 |
| 2006/0181548 | A1* | 8/2006 | Hafey et al. | 345/619 |
| 2006/0227969 | A1* | 10/2006 | Johnson et al. | 380/210 |
| 2006/0235716 | A1* | 10/2006 | Mahesh et al. | 705/1 |
| 2006/0244819 | A1* | 11/2006 | Pun et al. | 348/14.09 |
| 2007/0057865 | A1* | 3/2007 | Song et al. | 345/1.1 |
| 2007/0076245 | A1* | 4/2007 | Sugimoto et al. | 358/1.15 |
| 2007/0159457 | A1* | 7/2007 | Arthur | 345/156 |
| 2007/0159962 | A1* | 7/2007 | Mathavu et al. | 370/219 |
| 2007/0174429 | A1* | 7/2007 | Mazzaferri et al. | 709/218 |
| 2007/0198656 | A1* | 8/2007 | Mazzaferri et al. | 709/218 |
| 2007/0220161 | A1* | 9/2007 | Richey et al. | 709/231 |
| 2007/0222702 | A1* | 9/2007 | Toya | 345/1.1 |
| 2007/0244967 | A1* | 10/2007 | Ben-Shachar et al. | 709/204 |
| 2007/0273759 | A1* | 11/2007 | Krupnick et al. | 348/45 |
| 2007/0296643 | A1* | 12/2007 | Ben-Shachar et al. | 345/1.1 |
| 2007/0300220 | A1* | 12/2007 | Seliger et al. | 718/1 |
| 2008/0059598 | A1* | 3/2008 | Garibaldi et al. | 709/208 |
| 2009/0228801 | A1* | 9/2009 | Lee et al. | 715/730 |
| 2010/0245388 | A1* | 9/2010 | Bauch et al. | 345/634 |

OTHER PUBLICATIONS

Lee et al. Adapting Content for Mobile Devices in Heterogeneous Collaboration Environments. 2003. Department of Computer Science, Indiana University.*
Miura. A Framework for Transferring Desktop Images and Remote Operations in Multiple Computer Enviroments. 2003. Institute of Information Sciences and Electronics.*
WOLFVISION. "Visualizer and Telepathology—Remote Diagnosis with First-Class Imagery." 2006. Web.*
Specification to U.S. Appl. No. 60/871,774.*
Specification to U.S. Appl. No. 60/842,633.*
Sibomana et al., "Volumic Image Analysis Application Bundle for UNIX Workstations", 1996, IEEE, pp. 1488-1492.*
IBM Lotus Sametime 7.5—Lotus software LOD10754-USEN01 (4 pages).
http://www.webex.com/overview/online-meetings.html.
http://www.webex.com/overview/web-conferencing.html.
http://www.webex.com/overview/video-conferencing.html.
http://www.webex.com/overview/conference-calling.html.
http://www.webex.com/overview/webinars.html.
http://www.webex.com/overview/netmeeting-webex.html.
http://www.microsoft.com/windows/NetMeeting/Features/default.ASP.
http://www.microsoft.com/windows/NetMeeting/Features/Conferencing/default.ASP.
http://www.microsoft.com/windows/NetMeeting/Features/Chat/Default.ASP.
http://www.microsoft.com/windows/NetMeeting/Features/ILS/default.ASP.
http://www.microsoft.com/windows/NetMeeting/Features/Files/default.ASP.
http://www.microsoft.com/windows/NetMeeting/Features/appshare/default.asp.
http://www.microsoft.com/windows/NetMeeting/Features/RDS/default.ASP.
http://www.microsoft.com/windows/NetMeeting/Features/security/default.ASP.
http://www.microsoft.com/windows/NetMeeting/Features/Calls/default.ASP.
http://www.microsoft.com/windows/netmeeting/features/whiteboard/default.asp.

* cited by examiner

US 8,725,801 B2

SYSTEMS AND METHODS FOR IMAGE SHARING IN A HEALTHCARE SETTING WHILE MAINTAINING DIAGNOSTIC IMAGE QUALITY

BACKGROUND OF THE INVENTION

The present invention generally relates to methods and systems for sharing information. In particular, the present invention relates to methods and systems for sharing images and other information where image quality is maintained among various workstations.

In a clinical setting, patient information can be shared among multiple workstations. This type of information sharing streamlines health-care operations, facilitates distributed remote examination and diagnosis, and improves patient care.

Healthcare environments, such as hospitals or clinics, include storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system.

PACS connect to medical diagnostic imaging devices and employ an acquisition gateway (between the acquisition device and the PACS), storage and archiving units, display workstations, databases, and sophisticated data processors. These components are integrated together by a communication network and data management system.

A series or sequence of a plurality of medical images is an imaging study. In general, an imaging study that is the most recent imaging study of a patient or is the imaging study currently being examined by a practitioner will be referred to as a current imaging study.

In order to properly diagnose a current imaging study, a practitioner must examine one or more previously acquired images of the same patient and compare these images to images of a current study. An imaging study that includes two or more previously acquired images is an historical imaging study. Furthermore, an historical imaging study whose images are relevant for comparing with the images of a current imaging study is a comparison imaging study. For example, images that are associated with or display the same anatomy are relevant for comparison purposes.

A typical application of a PACS system is to provide one or more medical images for examination by a medical professional. For example, a PACS system can provide a series of x-ray images to a peer workstation where the images are displayed for a radiologist to perform a diagnostic examination. Based on the presentation of these images, the radiologist can provide a diagnosis. For example, the radiologist can diagnose a tumor or lesion in x-ray images of a patient's lungs.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper.

The quality of image is very important in clinical applications. Consistent presentation of images among various workstations is crucial to an accurate diagnosis.

Current collaboration systems, such as IBM® Lotus® Sametime®, allow remote workstation sharing capability. However, these technologies are not optimized for applications that involve the sharing of medical images.

U.S. Patent Application No. 2005/0267972 A1 by Costa-Requena et al., published on Dec. 1, 2005, refers to a method of exchanging user interface information over the Blocks Extensible Exchange Protocol (BEEP), for example. BEEP is a bidirectional application protocol that may use a single connection for data exchange, which allows for the preservation of resources.

However, exchanging data without maintaining the quality of images is not suitable for healthcare environments where an image may be used to make a diagnosis or determine a course of treatment.

The major problem with current collaboration systems in clinical applications that involve sharing medical images is the quality of images as displayed on the peer workstation(s).

For example, in clinical applications that involve sharing medical images, the peer workstation(s) often include monitors with different color depths than the monitors of the master workstation. A common problem with the evaluation of medical images and subsequent diagnosis based on those images is that the images may appear differently when viewed on a monitor of the peer workstation(s) as compared to a monitor of the master workstation.

For example, shared data may be displayed with the default lookup table of the peer workstation or a system-wide lookup table. Using these default or system-wide lookup tables may cause high-resolution images to be displayed incorrectly at the peer workstation.

The above example shows that image sharing between master and peer workstations with heterogeneous monitors often results in a loss of image quality. Maintenance of diagnostic image quality is imperative in a clinical setting. Therefore, a need exists for a mechanism to share images between heterogeneous master and peer workstations in clinical applications without loss of diagnostic image quality.

A typical master workstation may contain multiple monitors with different screen resolutions and color depths. For example, a master workstation may include a low resolution, 8-bit monitor and a high resolution, 24-bit monitor.

The different monitors of the master workstation may display different types of data. Generally, medical imaging workstations deal with at least two types of information: image data and non-image data.

Current collaboration systems do not distinguish image data and non-image data and may share only one monitor's screen resolution and color depth with the peer workstation. As a result, the quality of the high resolution, color images may deteriorate when displayed on peer workstation's monitor(s).

The above example shows that images shared by master workstations with mixed monitor configurations may result in degradation of image quality. Therefore, a need exists for a more efficient method for sharing images between master workstations with mixed monitor configurations and peer workstations.

BRIEF SUMMARY OF THE INVENTION

Certain embodiments of the present invention provide a method for image sharing and display. The method includes selecting an image, establishing a context with a peer workstation, and displaying an image on the peer workstation based on the established context. The context may include a sharing coordinate system, an indication of the type of data to be displayed, the coordinates of the data to be displayed, and lookup tables for data to be displayed.

Certain embodiments of the present invention provide a system for image sharing and display. The system includes a master workstation and a peer workstation. The peer workstation includes a display device adapted to display an image based at least in part on information received from the master workstation. The information received from the master workstation may include a sharing coordinate system, an indication of the type of data to be displayed, the coordinates of the data to be displayed, and lookup tables for data to be displayed.

Certain embodiments of the present invention provide a computer-readable storage medium. The computer-readable storage medium includes a set of instructions for execution on a computer. The set of instructions includes an initialization routine adapted to establishing a context between a master workstation and a peer workstation, a collaboration routine adapted to sharing data based at least in part on the established context, and a display routine adapted to displaying data using the established context. The context may include a sharing coordinate system, an indication of the type of data to be displayed, the coordinates of the data to be displayed, and lookup tables for data to be displayed.

Certain embodiments of the present invention provide a sharing coordinate system. The sharing coordinate system is a translation of the physical monitor configuration of the master workstation. The sharing coordinate system may be communicated from the master workstation to the peer workstation.

Figure 1:
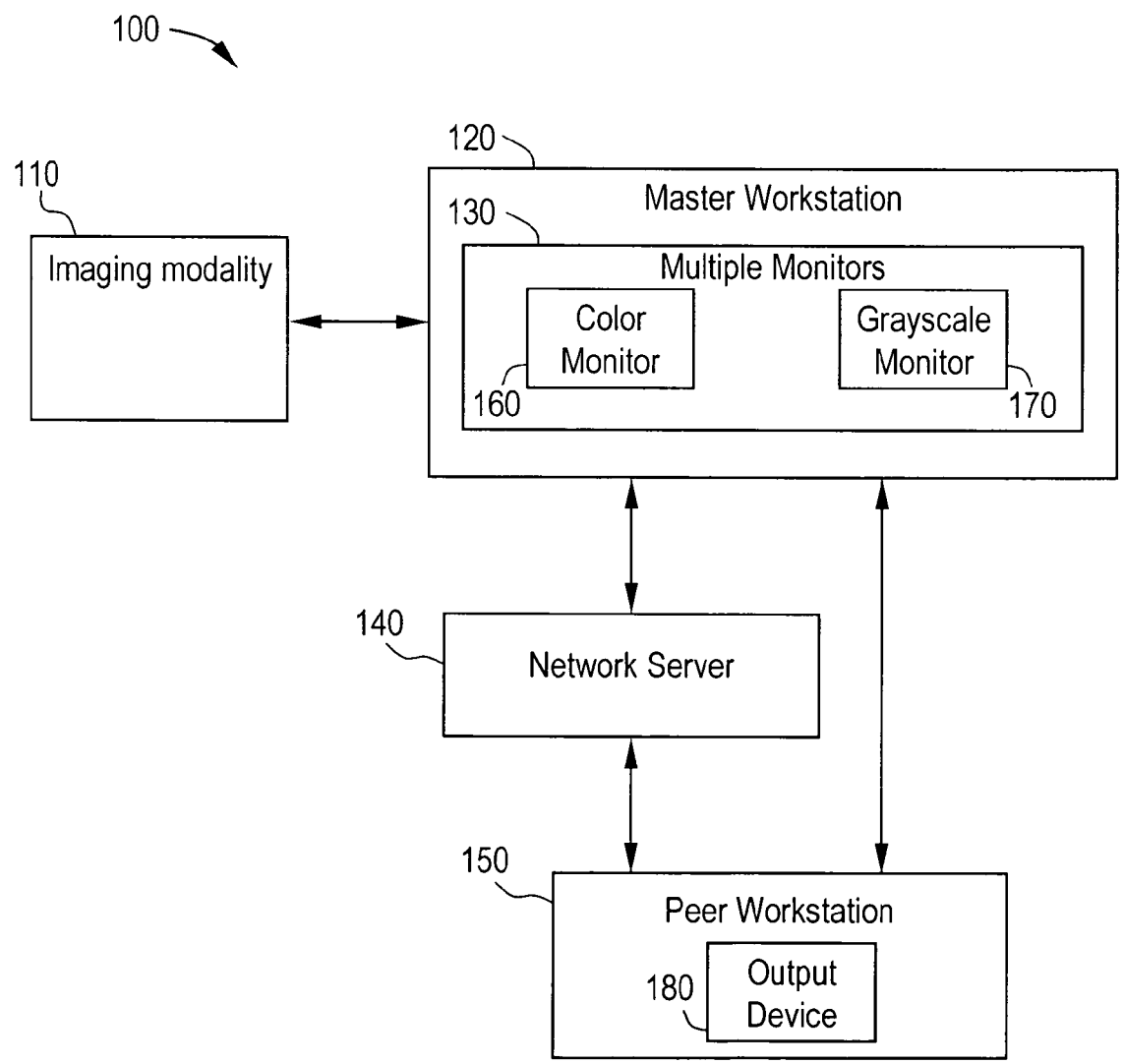
FIG. 1 illustrates an exemplary image sharing system according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE DRAWINGS

FIG. 1 illustrates an exemplary PACS system 100 according to an embodiment of the present invention. PACS system 100 includes an imaging modality 110, a master workstation 120, including multiple monitors 130, a network server 140 and at least one peer workstation 150. While system 100 is illustrated in FIG. 1 as including a single imaging modality 110, a single master workstation 120, a single network server 140, and a single peer workstation 150, system 100 can include any number of imaging modalities 110, master workstations 120, network servers 140, and/or peer workstations 150. In other words, no embodiment of the present invention is in any way limited to the illustration of system 100 as illustrated in FIG. 1.

The multiple monitors 130 of master workstation 120 may include, for example, a high resolution, color monitor 160 and a low resolution, grayscale monitor 170.

Certain embodiments of the invention may involve communication between various components 105. For example, imaging modality 110 is capable of communicating with master workstation 120. Master workstation 120 is capable of communicating with imaging modality 110 and server 140. Server 140 is capable of communicating with master workstation 120 and peer workstation 150. Peer workstation 150 is capable of communicating with server 140. In another embodiment of the present invention, master workstation 120 may also communicate directly with peer workstation 150.

Communication between various components 105 may occur over hardwired, wireless, or a combination of hardwired or wireless connections.

Peer workstation 150 includes an output device 180. The output device 180 may be an image display monitor or computer monitor, for example. Output device 180 may be, for example, a monitor with different resolution and color depth than any of the multiple monitors 130 of the master workstation 120.

In operation, imaging modality 110 obtains one or more images of a patient anatomy. Imaging modality 110 can include any device capable of capturing an image of a patient anatomy, such as a medical diagnostic imaging device. For example, imaging modality 110 can include am x-ray imager, ultrasound scanner, magnetic resonance imager, computed radiography/tomography imager, nuclear imager, or the like. Image data representative of the image(s) is communicated between imaging modality 110 and master workstation 120. The image data can be communicated electronically over a wired or wireless connection, for example.

Master workstation 120 may apply one or more preprocessing functions to the image data. The preprocessing functions may be employed to prepare the image(s) for viewing on one or more output devices 180 and/or to prepare the image(s) for storage at one or more of output devices 180 and server 140. For example, master workstation 120 may convert raw image data into a DICOM standard format or attach a DICOM header. In another example, a preprocessing function may include contrast or frequency preprocessing of an image.

Master workstation 120 may attach or associate image data attributes with the image(s). An image data attribute can include any electronically communicable data representative of information relevant to the image(s), patient, patient anatomy, and/or medical or imaging procedure, for example. Exemplary image data attributes include data representative of an imaging procedure, one or more DICOM tag(s) and/or one or more patient anatomies or mapped anatomies.

An image data attribute representative of an imaging procedure can include data representative of the procedures used to obtain the image(s) (to which the image data attribute is attached or associated). An imaging procedure can include a sequence of imaging steps used to obtain one or more images. For example, an imaging procedure can include the insertion of a contrast agent in a patient and then taking one or more images of the patient anatomy that includes the contrast agent. In another example, an imaging procedure may include the acquisition of one or more images without using any sort of contrast agent.

An imaging procedure may include the taking of one or more images of a certain patient anatomy. For example, an imaging procedure may identify which patient anatomy (such as a patient's head, neck or chest) is featured or shown in one or more images, for example.

An imaging procedure may also include the particular imaging modality used to obtain one or more images and/or particular type or class of imaging modality used to obtain one or more images. A particular imaging modality may be a certain or particular imaging modality device of a plurality of imaging modality devices. In another example, a particular type or class of imaging modality may be a C-arm x-ray imaging device, magnetic resonance ("MR") imaging device, etc.

An imaging procedure may also include a representation of a user that employed an imaging modality to obtain the image(s). For example, an imaging procedure may include a representation of an identity of a radiologist who used an MR imaging device to obtain the image(s).

An image data attribute may include data representative of one or more DICOM tags. A DICOM tag may be attached to or associated with image data by imaging modality 110 and/or master workstation 120. A DICOM tag may include any data specified by the DICOM Standard or any custom data allowed for by the DICOM Standard. For example, a DICOM tag may include image display data (e.g., (7FE0,0010) Pixel Data), image data characteristics (e.g., (0028,0002) Samples Per Pixel, (0028,0004) Photometric Interpretation), image capture characteristics (e.g., (0018,1050) Spatial Resolution, (0018,5101) View Position), anatomy data (e.g., (0018,0015) Body Part Examined), imaging device data (e.g., (0008,0060) Modality, (0008,1090) Manufacturer's Model Name), study-specific data (e.g., (0008,0020) Study Date, (0008,0030) Study Time), patient-specific data (e.g., (0010,0010) Patient's Name, (0010,0030) Patient's Birth Date), or any other data allowed for by the DICOM Standard.

An image data attribute may include data representative of a patient anatomy. Such data may include one or more mapped body parts. A mapped body part is any body part or anatomy featured in the image(s). An image data attribute that includes a mapped body part may be input by a user of system 100. For example, a radiologist may list or statically map the body part(s) or anatomy(ies) to be examined in an imaging procedure and/or featured in one or more images. Such a list may be attached to or associated with the image(s) as an image data attribute.

The display area of the master workstation 120 may be mapped into an image sharing coordinate system. A lookup table may be generated to map the color depth and resolution of the display area of the master workstation 120. The peer workstation 150 will display the display area of the master workstation based on the image sharing coordinate system and the associated lookup table.

Images (and associated image data attributes), an image sharing coordinate system, and the associated lookup table may then be communicated between master workstation 120 and server 140. The images (and associated image data attributes), an image sharing coordinate system, and associated lookup tables may be communicated over a wired or wireless connection.

Images (and associated image data attributes), an image sharing coordinate system, and associated lookup tables may be communicated between server 140 and peer workstation 150. The images (and associated image data attributes), an image sharing coordinate system, associated lookup tables may be communicated over a wired or wireless connection.

Server 140 can include any computer-readable storage and retrieval device that is accessible over an intranet or over the Internet. Server 140 can include a computer-readable storage medium suitable for storing the image data for later retrieval and viewing on a output device 180 at peer workstation 150.

Server 140 can also include a computer-readable storage medium suitable for storing one or more image sharing coordinate systems and lookup tables for data, as described in more detail below.

In another embodiment of the present invention, as described above, images (and associated image data attributes), an image sharing coordinate system, and lookup tables may be directly communicated between acquisition workstation 120 and peer workstation 150. The images (and associated image data attributes), an image sharing coordinate system, and lookup tables may be communicated over a wired or wireless connection.

A peer workstation 150 can include any device capable of displaying an imaging study. An imaging study may be used in a PACS system to make a diagnosis based on one or more images. For example, as described above, a radiologist using system 100 may employ a peer workstation 150 to analyze a series of images of a patient's lungs. The radiologist may use the images to determine whether the patient's lungs include a tumor.

As described above, peer workstation 150 can include any device capable of presenting an imaging study. For example, a peer workstation 150 includes an output device 180 in a PACS system. A peer workstation 150 can include a general purpose processing circuit, a network server 140 interface, a software memory, an input device (such as a keyboard, mouse, stylus, microphone, etc.) and an output device 180, for example. The network server 140 interface may be implemented as a network card connecting to a TCP/IP based network, but may also be implemented as a parallel port, USB, or FireWire interface, for example. While one exemplary output device 180 is described, this example should not be construed as limiting the present invention to just one output device 180. As described above, a output device 180 includes any device capable of presenting or displaying an imaging study to a user. Therefore, a output device 180 may also be embodied in a wireless output device, for example.

As described above, output devices 180 may receive image data (for example, an imaging study) from an master workstation 120 for display to one or more users. For example, an output device 180 may retrieve or receive an imaging study that includes a computed radiography ("CR") image of a patient's chest. A radiologist may then examine the image as displayed on a display device for any objects of interest such as, tumors, lesions, etc.

Output devices 180 may present one or more imaging studies according to a context sent by the master workstation 120. As described above, the context is a set of parameters for displaying image and non-image data on output device 180. For example, the context may include an image sharing coordinate system, the displayed data types, the coordinates of displayed data types, and/or lookup tables for the image data types. In general, the context may be employed to display a plurality of images on a display device 180 for a diagnostic examination of a patient anatomy featured in the images.

The context may direct, for example, a display device 180 to display image data based on the image sharing coordinate system and associated lookup tables.

Figure 2:
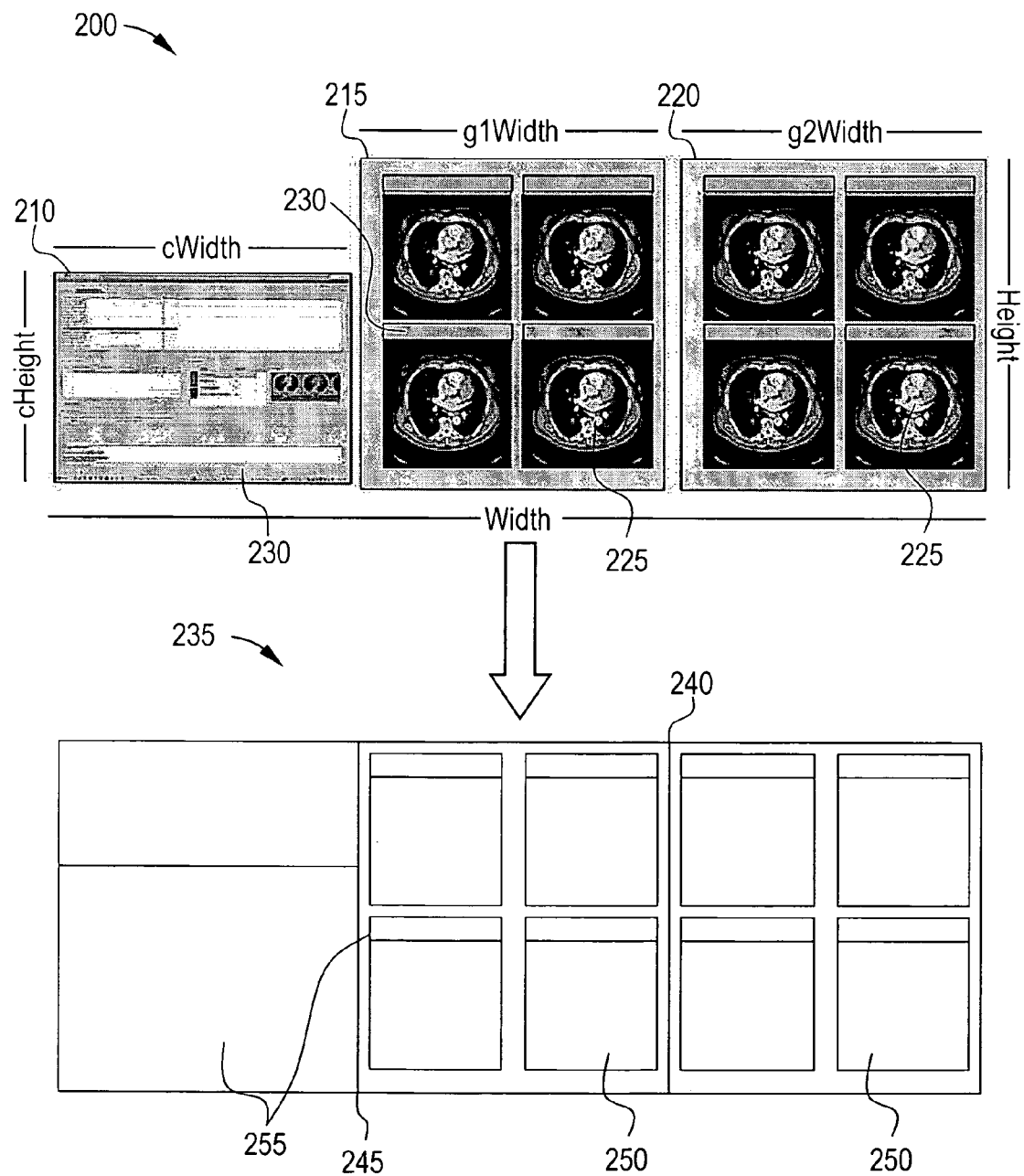
FIG. 2 depicts an exemplary translation of the physical monitor(s) of the master workstation into a image sharing coordinate system according to an embodiment of the present invention.

FIG. 2 illustrates is an exemplary master workstation 200, such as the master workstation 120 of the PACS system 100, according to an embodiment of the present invention. The master workstation 200 includes multiple monitors including, for example, a color monitor 210, a first grayscale monitor 215 and a second grayscale monitor 220, although any number of monitors 205 may be implemented. The monitors may display image data 225 or non-image data 230.

While the master workstation 200 is illustrated in FIG. 2 as including a single color monitor 210, a first grayscale monitor 215, a second grayscale monitor 220, and eight image regions 240 in the image sharing coordinate system 235, the 200 can include any number of color monitors 210, grayscale monitors 215 & 220, and image regions 240 in the image sharing coordinate system 235. In other words, no embodiment of the present invention is in any way limited to the illustration of master workstation 200 as illustrated in FIG. 2.

In certain embodiments of the present invention, the physical monitor configuration of the master workstation 200 may be translated into an image sharing coordinate system, such as the exemplary image sharing coordinate system 235.

For example, the color monitor 210, the first grayscale monitor 215 and the second grayscale monitor 220 of the master workstation 200 can be mapped into a single image sharing coordinate system 235.

As an example, the multiple monitors of the master workstation 200 may be a color monitor 210 with a screen resolution of 1280×1020, the first grayscale monitor 215 with a screen resolution of 1200×1600, and the second grayscale monitor 220 with a screen resolution of 1200×1600. The width, height of the image sharing coordinate system 235 would be 3680×1600.

The image sharing coordinate system 235 may begin at the lower left with (0,0) and end at the upper right with (width, height). For example, the upper right corner of the first grayscale monitor 215 is assigned coordinate (cWidth+g1Width, Height) 240 and the lower right corner of the color monitor 210 is assigned coordinate (cWidth, 0) 245.

The image sharing coordinate system 235 may divided into regions for image and non-image data types. For example, the image sharing coordinate system 235 may consist of image regions 250 that correspond to image data 225. The image sharing coordinate system 235 may also consist of non-image regions 255 that correspond to non-image data 230.

Example 1

Image Sharing Initialization

As an example, the following information may be sent to the client workstation 150 upon initialization:

```
<Initialization>
    <VirtualScreen>
        <Width>3680</Width>
        <Height>1600</Height>
        <Screen id=1>
            <Width>1280</Width>
            <Height>1024</Height>
            <Type>32 Bit Tru Color</Type>
        <Screen>
        <Screen id=2>
            <Width>1200</Width>
            <Height>1600</Height>
            <Type>8 Bit Gray</Type>
        <Screen>
        <Screen id=3>
            <Width>1200</Width>
            <Height>1600</Height>
            <Type>8 Bit Gray</Type>
        <Screen>
    </VirtualScreen>
</Initialization>
```

As discussed above, the components, elements, and/or functionality of the system 600 may be implemented alone or in combination in various forms in hardware, firmware, and/ or as a set of instructions in software, for example. Certain embodiments may be provided as a set of instructions residing on a computer-readable medium, such as a memory, hard disk, DVD, or CD, for execution on a general purpose computer or other processing device.

Figure 3:
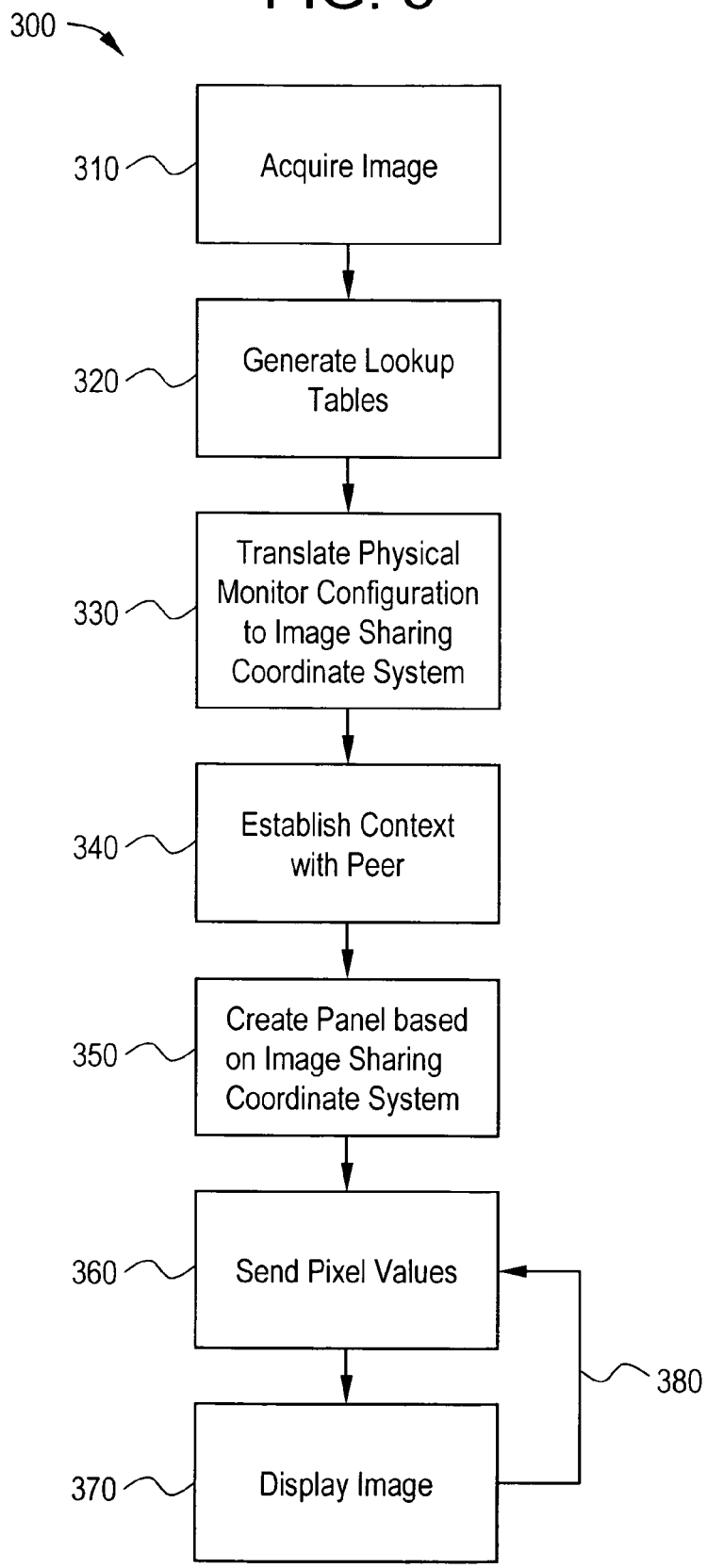
FIG. 3 illustrates an exemplary method for sharing and displaying images according to an embodiment of the present invention.

FIG. 3 illustrates an image display method 300 according to an embodiment of the present invention. The image display method 300 includes the following steps, which are described below in more detail. At step 310, an image set is acquired. At step 320, lookup tables are generated. At step 330, the physical monitor configuration of the master workstation is translated to an image sharing coordinate system. At step 340, a context is established between the master workstation and the peer workstation. At step 350, the peer workstation creates a panel based on the image sharing coordinate system. At step 360, the master workstation sends out the pixel values of the displayed area of the master workstation. At step 370, the pixels are painted in the peer workstation based on the lookup tables. At step 380, the master workstation may propagate changes made in the image or non-image data by region.

At step 310, an image set is acquired. The image set may be acquired by the PACS system 100. More particularly, the image set may be acquired by the imaging modality 110 of the PACS system 100. The image set may include one or more images.

In certain embodiments of the present invention, the image may be reacquired manually, for example, by a user, such as a surgeon, a nurse, a technician, and/or another user. In certain embodiments of the present invention, the image may be reacquired automatically, for example, by an endoscope, an endoscopic system, and/or another imaging system.

At step 320, lookup tables may be generated to map the color depth and resolution of the display area of the master workstation. Using lookup tables to store color information in a sharing environment is advantageous because the amount of storage space necessary is drastically reduced allowing for faster processing and communication speeds.

At step 330, the physical monitor configuration of the master workstation is translated to a coordinate system, for example image sharing coordinate system 235. For example, multiple mixed configuration monitors such as the color monitor 210, the first grayscale monitor 215 and the second grayscale monitor 220 of the master workstation 200, may be translated into a single image sharing coordinate system 235. Alternatively, a single monitor at the master workstation 200 may be translated into a single image sharing coordinate system.

At step 340, a context is established between the master workstation 120 and the peer workstation 150. The context may include the image sharing coordinate system 235, the displayed data types, the coordinates of displayed data types, and lookup tables for image data types. The context may be communicated electronically to the peer workstation 150 over a wired or wireless connection, for example.

At step 350, the peer workstation 150 creates a panel based on the image sharing coordinate system 235. If the peer workstation 150 includes an output device 180 with the required resolution, a screen can be displayed on that output device 180. If there is no output device 180 that can accommodate the panel, a large panel will be created that requires paging between the panels.

At step 360, the master workstation 120 sends out the pixel values of the displayed areas of the master workstation 120. The pixel values may be communicated electronically to the peer workstation 150 over a wired or wireless connection, for example.

At step 370, the pixels will be painted in the peer workstation based on the context sent at step 340. Once the peer workstation 150 receives the pixel values in the image sharing coordinate system 235, the pixels will be painted based on the image coordinate system 235 and associated lookup tables for the non-image and image data types. This ensures that the image pixels painted in the peer workstation 150 have the same lookup table value as in the master workstation 120.

At step 380, master workstation 120 may propagate changes made in the image or non-image data by region.

In one embodiment of the current invention, computer readable instructions at the master workstation 120 can generate the lookup table, create the image sharing coordinate system 235, and transmit the context and data to be displayed to peer workstation 150.

In another embodiment of the current invention, a user may change the image displayed in one or more of the image regions 250 on output device 180. In this case, the master workstation 120 will send the updates or changes only for the region(s) affected.

For example if a clinician desires to compare an image from a current imaging study to an image from a comparison imaging study and only one image region 250 is being updated, the peer workstation 150 will receive updates only for that region.

Example 2

Screen Update

As an example, the following information may be sent to the client workstation 150 to update one or more image regions 250:

```
<Screen Update>
  <Screen id=1>
    <Region x=0 y=0 width=1280 height=1024>
      <Type>NonImage</Type>
      <Data>Bitmap</Data>
      <LookupTable>ColorLookupTable</LookupTable>
    <Region>
  </Screen>
  <Screen id=2>
    <Region x=0 y=0 width=1280 height=30>
      <Type>NonImage</Type>
      <Data>Bitmap</Data>
      <LookupTable>GrayScaleLookupTable </LookupTable>
    <Region>
    <Region x=0 y=30 width=600 height=770>
      <Type>Image</Type>
      <Data>Bitmap</Data>
      <LookupTable>GrayScaleImageLookupTable </LookupTable>
    <Region>
    ...
  </Screen>
  <Screen id=3>
    <Region x=0 y=0 width=1280 height=30>
      <Type>NonImage</Type>
      <Data>Bitmap</Data>
      <LookupTable>GrayScaleLookupTable </LookupTable>
    <Region>
    <Region x=0 y=30 width=600 height=770>
      <Type>Image</Type>
      <Data>Bitmap</Data>
      <LookupTable>GrayScaleImageLookupTable</LookupTable>
    <Region>
    ...
  </Screen>
</Screen Update>
```

The ColorLookupTable, GrayScaleLookupTable and GrayScaleImageLookupTable may be exchanged before painting the pixels on the peer workstation.

One or more of the steps 310-380 of the method 300 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any image sharing system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A method for sharing diagnostic quality images between a master workstation and one or more peer workstations in a healthcare environment, the method including:
   generating lookup tables for a master workstation, the lookup tables mapping a color depth that contains information to produce the exact same appearance of an image on other monitor(s) with different display characteristics and a resolution of a display area of the master workstation, and the display area of the master workstation comprises a plurality of monitors;
   translating a physical monitor configuration of the plurality of monitors of the master workstation to a single coordinate system for the master workstation;
   communicating a context from the master workstation to a peer workstation, the context including the single coordinate system for the master workstation and the lookup tables for the master workstation;
   and communicating a plurality of pixel values corresponding to medical imaging data from the master workstation to the peer workstation;
   painting a display area of the peer workstation with the plurality of pixel values based on the single coordinate system for the master workstation and the lookup tables for the master workstation and
   wherein the physical monitor configuration of the plurality of monitors of the master workstation comprises a first monitor with a first resolution and a second monitor with a second resolution different than the first resolution.

2. The method of claim 1, further including propagating changes to the display area of the master workstation to the peer workstation during a collaboration session by updating the single coordinate system for the master workstation and the lookup tables for the master workstation and repainting the display area of the peer workstation using the updated single coordinate system and lookup tables.

3. The method of claim 1, wherein said context further includes an indication of the data type as non-image data or image data.

4. The method of claim 2, wherein regions are created in the single coordinate system for the image and non-image data types.

5. The method of claim 3, wherein the master workstation propagates changes made in the data by said regions.

6. The method of claim 1, further including the step of acquiring an image.

7. A system for sharing diagnostic quality images in a healthcare environment, the system including:
   a master workstation and one or more peer workstations,
   wherein lookup tables for a master workstation, the lookup tables mapping a color depth that contains information to produce the exact same appearance of an image on other monitor(s) with different display characteristics and a resolution of a display area of the master workstation, and the display area of the master workstation comprises a plurality of monitors;
   wherein a physical monitor configuration of the plurality of monitors of the master workstation is translated into a single coordinate system;
   wherein a context is communicated from the master workstation to a peer workstation, the context including the single coordinate system for the master workstation and the lookup tables for the master workstation;

and a plurality of pixel values corresponding to medical imaging data from the master workstation is communicated to the peer workstation;

painting a display area of the peer workstation with the plurality of pixel values based on the single coordinate system for the master workstation and the lookup tables for the master workstation and wherein the physical monitor configuration of the plurality of monitors of the master workstation comprises a first monitor with a first resolution and a second monitor with a second resolution different than the first resolution.

8. The system of claim 6, wherein the information received from the master workstation includes an indication of the data type as non-image data or image data.

9. The system of claim 6, further including an imaging modality to acquire the image.

10. The system of claim 6, wherein the master workstation can communicate directly with said one or more peer workstations.

11. The system of claim 6, further including a network server configured to facilitate communication between the master workstation and the peer workstation.

12. The system of claim 6, wherein the master workstation is configured to modify the image.

13. The system of claim 6, wherein the plurality of monitors of the master workstation are of mixed configurations.

14. The system of claim 6, wherein the system is a picture archiving and communication system.

15. A non-transitory computer-readable storage medium including a set of instructions for a computer, the set of instructions including:

an initialization routine configured to communicate a context from a master workstation to one or more peer workstations, wherein the context includes lookup tables for a master workstation, the lookup tables mapping a color depth which contains information to produce the exact same appearance of an image on other monitor(s) with different display characteristics and a resolution of a display area of the master workstation, the display area of the master workstation comprising a plurality of monitors, and wherein the context includes a single coordinate system for the plurality of monitors of the master workstation, the single coordinate system providing a physical monitor configuration of the plurality of monitors of the master workstation;

a collaboration routine configured to share diagnostic quality medical images; and a display routine configured to display shared medical images at the one or more peer workstations based on said lookup tables for the master workstation and said single coordinate system for the master workstation.

16. The non-transitory computer-readable storage medium of claim 14, the set of instructions further including a data selection routine configured to select images to be shared with said peer workstations.

17. The non-transitory computer-readable storage medium of claim 14, the set of instructions further including an update routine configured to make updates to the shared image.

* * * * *